(12) United States Patent
Kubohara et al.

(10) Patent No.: US 7,846,974 B2
(45) Date of Patent: Dec. 7, 2010

(54) METHOD OF LOWERING BLOOD GLUCOSE AND METHOD OF TREATING DIABETES AND OBESITY

(75) Inventors: Yuzuru Kubohara, Maebashi (JP); Hiroshi Shibata, Maebashi (JP)

(73) Assignee: National University Corporation Gunma University, Maebashi-shi, Gunma (JP)

( * ) Notice: Subject to any disclaimer, the term of this patent is extended or adjusted under 35 U.S.C. 154(b) by 36 days.

(21) Appl. No.: 11/923,064

(22) Filed: Oct. 24, 2007

(65) Prior Publication Data

US 2009/0111893 A1     Apr. 30, 2009

(51) Int. Cl.
*A61K 31/05* (2006.01)
*A61K 31/045* (2006.01)

(52) U.S. Cl. ............... 514/734; 514/728; 514/866; 514/909

(58) Field of Classification Search ............... 514/183, 514/866, 909, 728, 734
See application file for complete search history.

(56) References Cited

U.S. PATENT DOCUMENTS

2004/0259244 A1* 12/2004 Scharp et al. ............... 435/366

FOREIGN PATENT DOCUMENTS

JP         2006290810 A  * 10/2006

OTHER PUBLICATIONS

Omata et al., "Dictyostelium differentiation-inducing factor-1 induces glucose transporter 1 translocation and promotes glucose uptake in mammalian cells", The FEBS Journal, vol. 274. pp. 3392-3404 (2007).*
JP 2006290810 A, hereby known as Kubohara et al., enclosed English abstract.*

* cited by examiner

*Primary Examiner*—Kevin Weddington
(74) *Attorney, Agent, or Firm*—Knobbe, Martens, Olson & Bear, LLP

(57) ABSTRACT

The compound represented by the general formula (I) is administered to a subject suffering from diabetes or obesity.

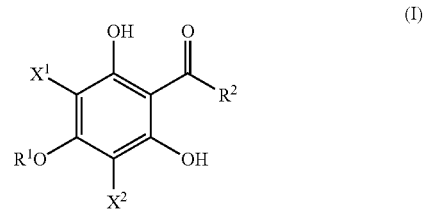

In the formula (I), $R^1$ and $R^2$ independently represent an aliphatic hydrocarbon group having 1 to 10 carbon atoms or phenyl group, and arbitrary hydrogen atoms on the aliphatic hydrocarbon group and the phenyl group may be replaced by halogen, $X^1$ represents halogen, and $X^2$ represents hydrogen or halogen.

3 Claims, 7 Drawing Sheets

METHOD OF LOWERING BLOOD GLUCOSE AND METHOD OF TREATING DIABETES AND OBESITY

FIELD OF INVENTION

The present invention relates to a method of lowering blood glucose level and a method of preventing or treating diseases including obesity and diabetes.

BACKGROUND OF INVENTION

Diabetes is one of so-called "lifestyle-related diseases", and the number of patients has been increasing these days. Diabetes is caused by deficiency in function of regulation of blood glucose level, and chronic high blood glucose level leads to neuropathy in peripheral nerves and angiopathy, and finally leads to loss of sight and necrosis.

Insulin, a hormone to lower blood glucose level, is used as an anti-diabetic drug, but insulin is administered via injection, which burdens patients. Moreover, diabetes for which insulin is not effective is also known, and definite remedy has not been developed although some drugs to improve symptoms exist. Thus, anti-diabetic drug which is more effective and can be orally administered is desired to be developed.

Recently, obesity has also been a problem as one of causes for various lifestyle-related diseases, and effective agents for improving or treating obesity is desired to be developed. It is postulated that obesity is caused by impaired glucose tolerance, a condition where blood glucose level temporary increases after food intake and decreases slowly, and that improvement of the impaired glucose tolerance is effective for preventing or treating obesity.

The compound (A) shown below is called DIF-1 and was isolated from a cellular slime mold, and is known to have anti-cancer activity (Biochem Biophys Res Commun. 1997 Jul. 18; 236(2):418-22). However, it has not been known that DIF-1 and its related compounds have an activity to promote the glucose uptake of cells and an activity to lower blood glucose.

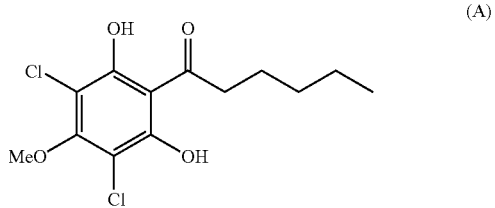

(A)

DISCLOSURE OF INVENTION

The present invention aims to provide a novel glucose uptake-promoting agent. The present invention also aims to provide a method for lowering blood glucose level and a method for preventing or treating diabetes and obesity by administering the glucose uptake-promoting agent.

The inventors of the present invention assiduously studied to solve the above-mentioned problem, and found that the compound known as DIF-1 and its related compounds have a significant glucose uptake-promoting activity in various cells and thus the compounds can be used as blood glucose-lowering agent, thereby completed the present invention.

An object of the present invention is to provide a method of lowering blood glucose level in a subject, comprising administering a compound represented by the formula (I) to the subject.

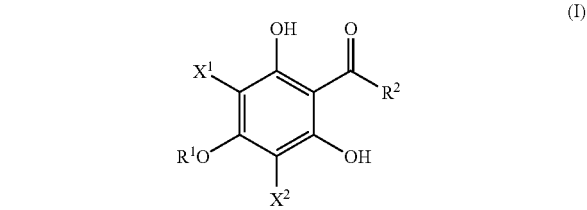

(I)

In the formula (I), $R^1$ and $R^2$ independently represent an aliphatic hydrocarbon group having 1 to 10 carbon atoms or phenyl group, and arbitrary hydrogen atoms on the aliphatic hydrocarbon group and the phenyl group may be replaced by halogen, $X^1$ represents halogen, and $X^2$ represents hydrogen or halogen.

Another object of the present invention is to provide a method of preventing or treating obesity and/or diabetes in a subject, comprising administering a compound represented by the formula (I) to the subject to ameliorate a symptom of the subject.

DESCRIPTION OF THE PREFERRED EMBODIMENTS

Figure 1:
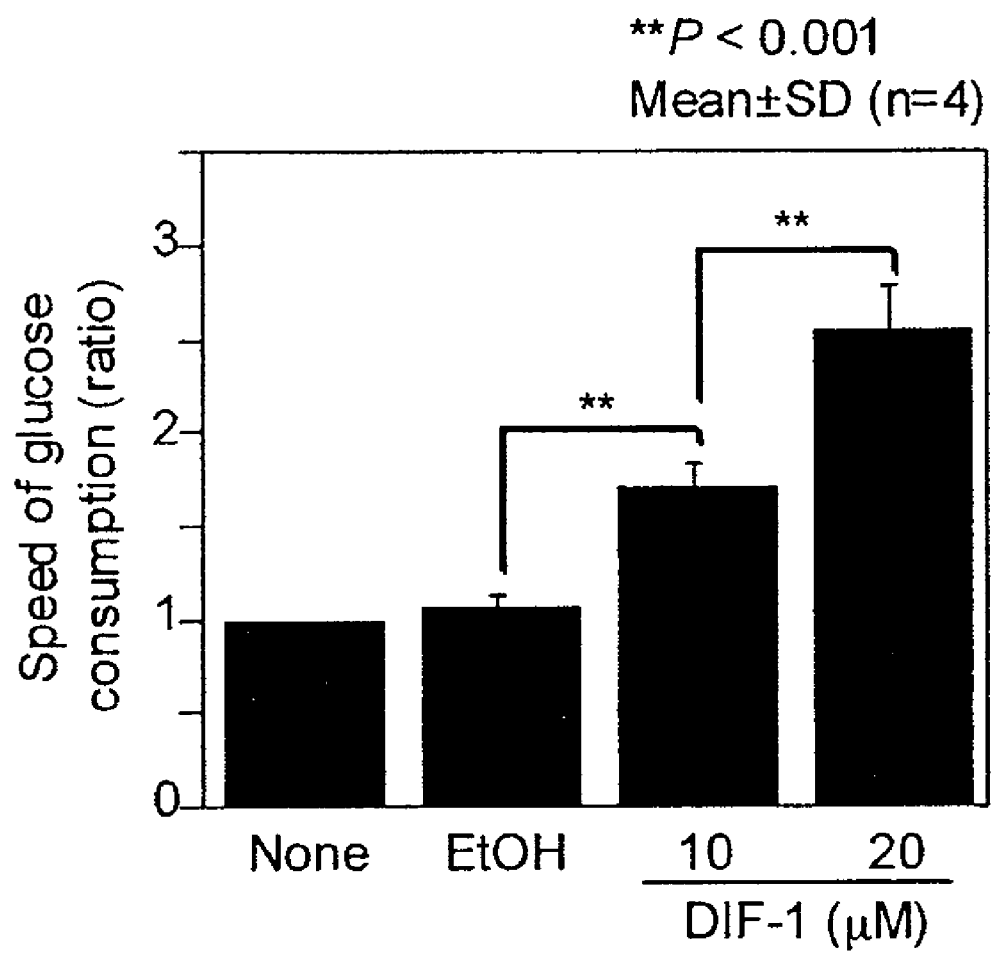
FIG. 1 is the first drawing that shows the glucose uptake rate of 3T3-L1 cells when 3T3-L1 cells were cultured in the presence of DIF-1.

Hereinafter, the present invention is described in detail.

<1> Glucose Uptake-Promoting Agent of the Present Invention

The glucose uptake-promoting agent of the present invention comprises the following compound as an active ingredient.

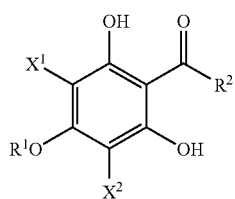
(I)

In the formula (I), $R^1$ represents an aliphatic hydrocarbon group or phenyl group, and arbitrary hydrogen atoms on the aliphatic hydrocarbon group and the phenyl group may be replaced by halogen. The aliphatic hydrocarbon group has 1 to 10 carbon atoms, preferably has 1 to 8 carbon atoms, and more preferably has 1 to 5 carbon atoms. The aliphatic hydrocarbon group may be linear or branched, and may also contain a cyclic structure. The aliphatic hydrocarbon group may also have one or more double bond(s) or triple bond(s). $R^1$ is preferably an alkyl group having 1 to 10 carbon atoms or phenyl group, and more preferably an alkyl group having 1 to 8 carbon atoms or phenyl group, and further more preferably an alkyl group having 1 to 5 carbon atoms or phenyl group.

$R^2$ represents an aliphatic hydrocarbon group or phenyl group, and arbitrary hydrogen atoms on the aliphatic hydrocarbon group and the phenyl group may be replaced by halogen. The aliphatic hydrocarbon group has 1 to 10 carbon atoms, preferably has 2 to 8 carbon atoms, and more preferably has 3 to 7 carbon atoms. The aliphatic hydrocarbon group may be linear or branched, and may also contain a cyclic structure. The aliphatic hydrocarbon group may also have one or more double bond(s) or triple bond(s). $R^2$ is preferably an alkyl group having 1 to 10 carbon atoms or phenyl group, and more preferably an alkyl group having 2 to 8 carbon atoms or phenyl group, and further more preferably an alkyl group having 3 to 7 carbon atoms or phenyl group.

$X^1$ is halogen, and specifically chlorine, bromine, or fluorine, and preferably chlorine.

$X^2$ is halogen or hydrogen, and specifically chlorine, bromine, fluorine or hydrogen, and preferably chlorine or hydrogen.

Example compounds from the formula (I) are shown below. But the formula (I) is not limited to these compounds.

DIF-1

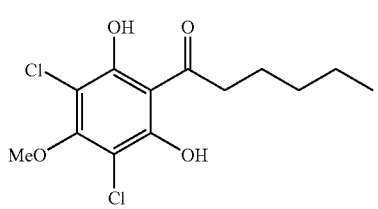

Other Derivative Compounds

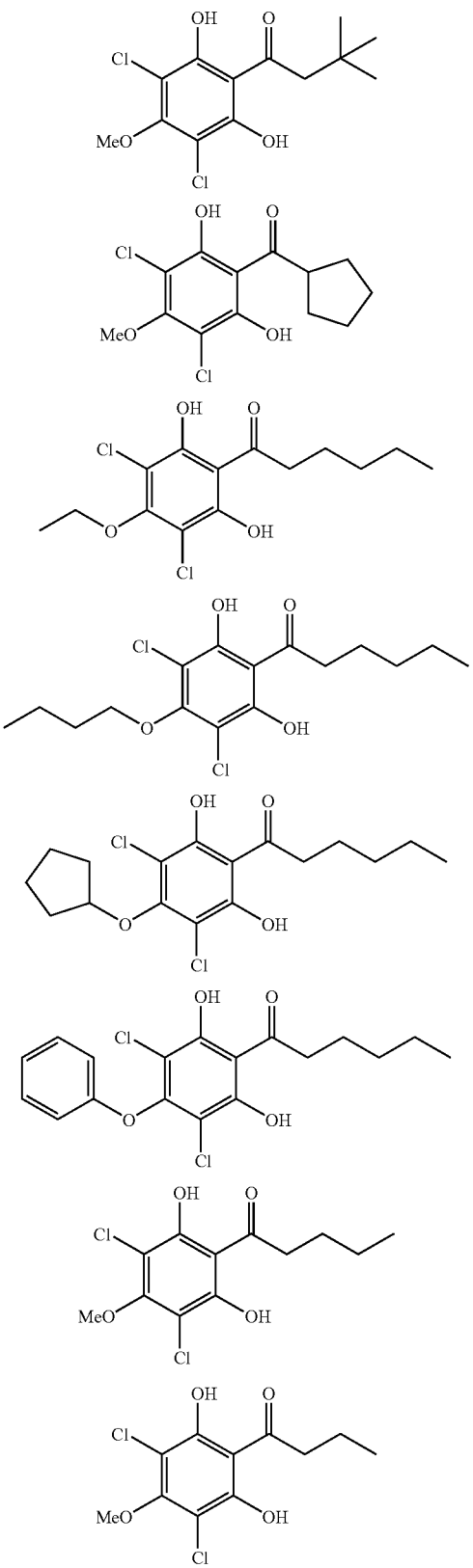

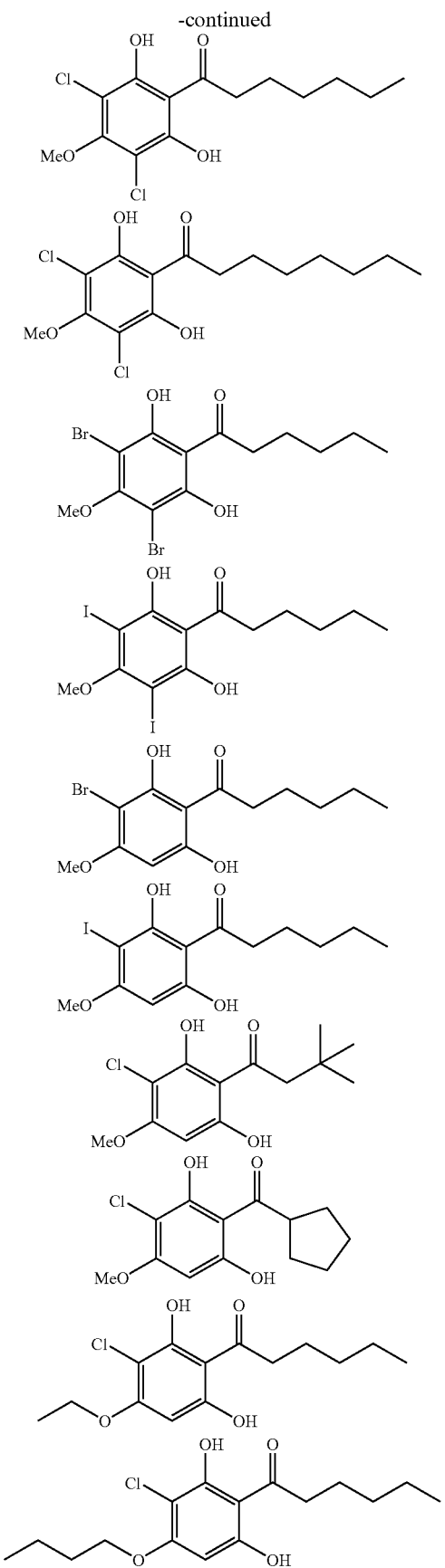

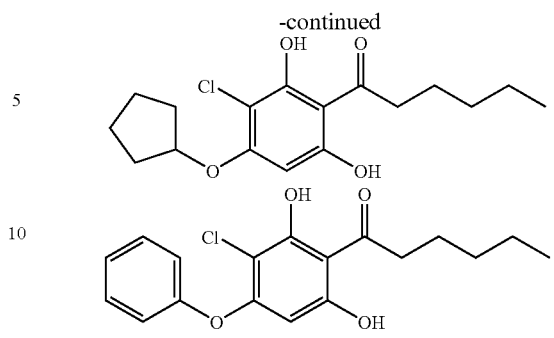

Other Derivative Compounds—Continued

The compounds of the formula (I) can be synthesized according to conventional chemical synthesis methods. For example, methods of synthesizing DIF-1 and its related compounds are disclosed in Biochem. J. 1988 Nov. 15:256(1):23-8.

The compounds may be commercially available.

The compounds of formula (I) possess a glucose uptake-promoting activity in various kinds of cells, and therefore, can be used as a blood glucose-lowering agent as well as a drug to treat or prevent diseases such as diabetes and obesity.

A medicament comprising the compounds, singly or in combination with a pharmaceutical acceptable carrier, can be safely administered orally or parenterally (for example, local administration, rectal administration or intravenous administration) as a form of pill (including sugarcoating pill and filmcoating pill), powder, granule, capsule (including soft capsule), liquid, injection, suppository, sustained preparation and the like, according to known methods generally used in production of pharmaceuticals.

The compounds may be contained in the medicaments at the concentration range of about 0.01 to about 100 weight % with respect to the whole amount of the medicament.

Doses of the compounds depend on the subject to be administered, symptoms, administration methods, and so on, and are not particularly limited. Generally, in the case of a subject having weight of 60 kg, the compounds are administered about 0.1 to 100 mg per day, preferably about 1.0 to 50 mg per day, and more preferably about 1.0 to 20 mg per day. Examples of diabetic subjects include those showing blood glucose level of 200 mg/dl or more two hours after food intake. Examples of obesity subjects include those showing BMI (Body mass index) of 26 or more.

Examples of pharmaceutical acceptable carrier include diluents, smoothing agent, binding agent, and disintegrant for solid preparation; and solvent, solubilizing agent, suspending agent, buffer, and soothing agent for liquid preparation. If necessary, antiseptic, antioxidant, coloring agent, sweetening agent, absorbing agent, and moistening agent may be added in an appropriate amount. Examples of diluents include lactose, saccharose, D-mannitol, starch, cornstarch, crystallized cellulose, light anhydrous silicic acid. Examples of smoothing agents include magnesium stearate, calcium stearate, talc, and, colloid silica. Examples of binders include crystallized cellulose, sucrose, D-mannitol, dextrin, hydroxypropyl cellulose, hydroxypropylmethyl cellulose, polyvinylpyrrolidone, starch, sucrose, gelatin, methylcellulose, carboxymethylcellulose sodium. Examples of disintegrants include starch, carboxymethylcellulose, carboxymethylcellulose calcium, carboxymethyl starch sodium, and L-hydroxypropyl cellulose. Examples of solvents include water for injection, alcohol, propyleneglycol, macrogol, sesame oil, corn oil, and olive oil. Examples of solubilizing agents include polyethylene glycol, propylene glycol, D-mannitol, benzyl benzoate, ethanol, Tris aminomethane, cholesterol, triethanolamine, sodium carbonate, and sodium citrate. Examples of suspending agents include detergents such as stearyl triethanolamine, sodium lauryl sulfate, lauryl amino propionate, lecithin, benzalkonium chloride, benzethonium chloride, glyceryl monostearate; hydrophilic polymer such as polyvinyl alcohol, polyvinylpyrrolidone, carboxymethylcellulose sodium, methylcellulose, hydroxymethylcellulose, hydroxyethylcellulose, and hydroxypropylcellulose. Examples of tonicity agents include glucose, D-sorbitol, sodium chloride, glycerol, and D-mannitol. Examples of buffers include phosphate salt, acetate salt, carbonate salt, citrate salt. Examples of soothing agents include benzylalcohol. Examples of antiseptics include para-hydroxybenzoic acid ester, chlorobuthanol, benzylalcohol, phenethyl alcohol, dehydro acetate, and sorbic acid. An example of an antioxidant includes salt of sulfurous, ascorbic acid, and alpha-tocopherol.

The glucose uptake-promoting agents of the present invention may be combined with other anti-diabetic drugs such as insulin.

EXAMPLES

Hereinafter, the present invention will be described with reference to Examples. However, the present invention is not limited to the Examples.

Example 1

Glucose Uptake-Promoting Effect of DIF-1 in 3T3L1 Cells (1) Mouse 3T3-L1 fibroblasts were cultured in 1 ml of a suitable medium (contained in a 12-well plastic dish) for several days until the cells reached confluence. Then, the cells were cultured for 10-12 hours in the nutrition medium (None), the nutrition medium to which only 0.2% ethanol, a solvent of DIF-1, was added (EtOH), and the nutrition medium to which 10 or 20 M DIF-1 dissolved in ethanol was added, respectively, and then, glucose concentration in each of the media was determined, based on which glucose uptake rate of the cells was calculated and the ratio with respect to the control was plotted (FIG. 1). As a result, it was found that, in the presence of DIF-1, the glucose uptake ratio of the cell increased dependently on DIF-1 concentration. The data of FIG. 1 are shown by mean value and standard deviation (Bars) of four independent experiments (n=4).

Figure 2:
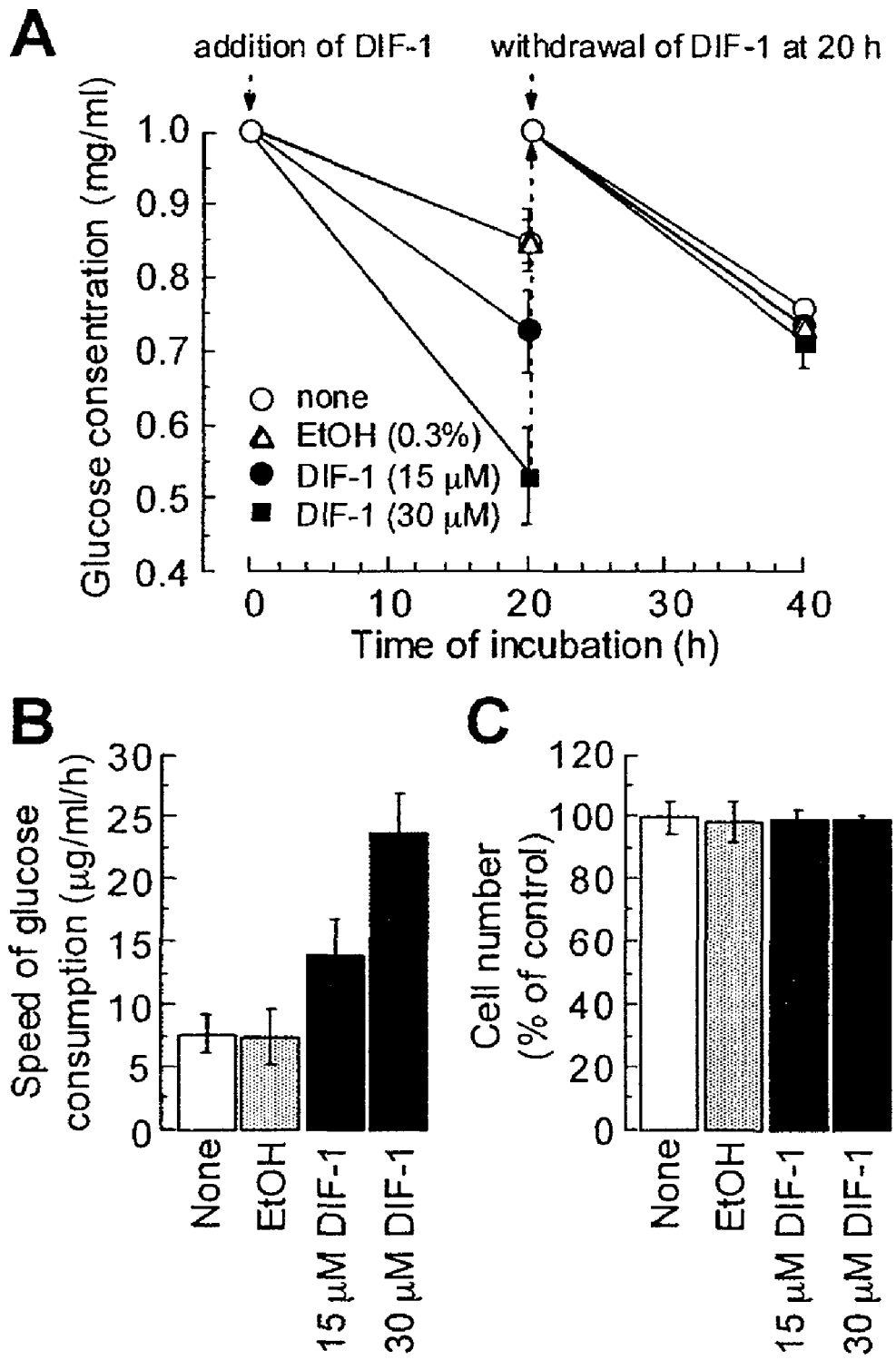
FIG. 2 is the second drawing that shows the glucose uptake rate of 3T3-L1 cells when 3T3-L1 cells were cultured in the presence of DIF-1. Graph A shows the glucose concentration in the medium after 20-hour-culture with no addition, with addition of ethanol, or addition of DIF-1, and after further 20-hour-culture (total 40-hour-culture) in a DIF-1-free medium. Graph B shows the glucose uptake rate of each kind of the cells after the 20-hour-culture and graph C shows the number of cells after the 40-hour-culture.

(2) Then, mouse 3T3L1 fibroblasts were cultured in 1 ml of a suitable medium (contained in a 12-well plastic dish) until the cells reached confluence. After changing the medium to a new medium (this time point corresponds to 0 hour in the graph), DIF-1 was added, and glucose concentration in the medium was measured at the time point of 20 hours (FIG. 2A), based on which glucose consumption rate was calculated (FIG. 2B). Then, the media were changed to new media containing no DIF-1 for all the samples, and after culture was continued for another 20 hours, glucose concentration was measured (FIG. 2A). The number of cells at this time point was also determined (FIG. 2C). The data of the graph are mean values and standard deviations (Bars) (n=3) of the results of triplicate samples evaluated under the same conditions.

It was found from these results that DIF-1 promotes glucose uptake of cells in a concentration-dependent manner without influencing the number of cells (FIG. 2C). It was also found that the action of DIF-1 is reversible and glucose uptake of the cells returned to the original state when DIF-1 was removed during culture (FIG. 2A). According to microscopic observation, cell morphology did not changed and cell damage was not observed in the presence of DIF-1.

Example 2

Figure 3:
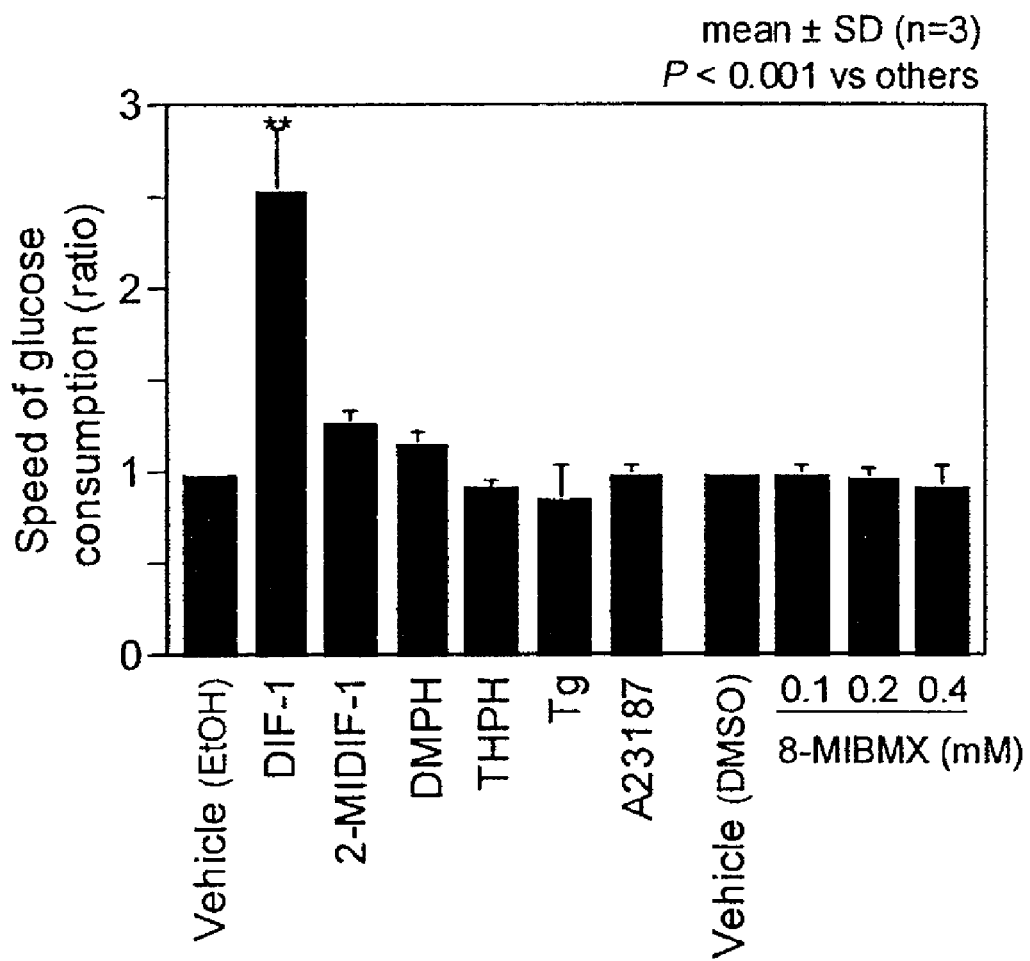
FIG. 3 is a drawing that shows the effects of DIF-1, and its artificial derivatives (2-MIDIF1, DMPH, and THPH), Tg, A23187, or 8-MIBMX on the glucose uptake rate of 3T3-L1 cells.

Glucose uptake-promoting activity of DIF-1 and its artificial derivatives (2-MIDIF1, DMPH, THPH) were compared in the same condition as Example 1 (FIG. 3). The data of the graph are mean values and standard deviations (Bars) (n=3) of three independent experiments.

Interestingly, DIF-1 derivatives shown below did not substantially have glucose uptake-promoting activity, and it is found that glucose uptake-promoting activity of DIF-1 is specific to its chemical structure. Furthermore, although DIF-1 is known to increase intracellular calcium concentration and intracellular cyclic AMP concentration, Tg (Thapsigargin) and A23187, both of which are agents to increase intracellular calcium, and 8-MIBMX, which is an agent to increase intracellular cyclic AMP, did not promote glucose uptake. Therefore, it was found that the glucose uptake-promoting effect by DIF-1 is a novel phenomenon which is independent from increase of intracellular calcium and intracellular cyclic AMP.

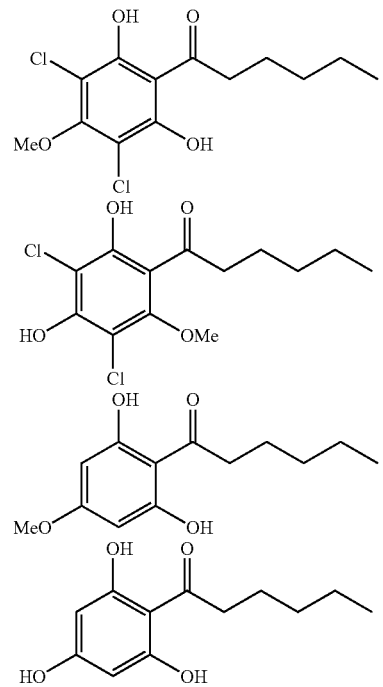

upper left: DIF-1, upper right: 2MIDIF-1, lower left: DMPH, and lower right: THPH Example 3

Figure 4:
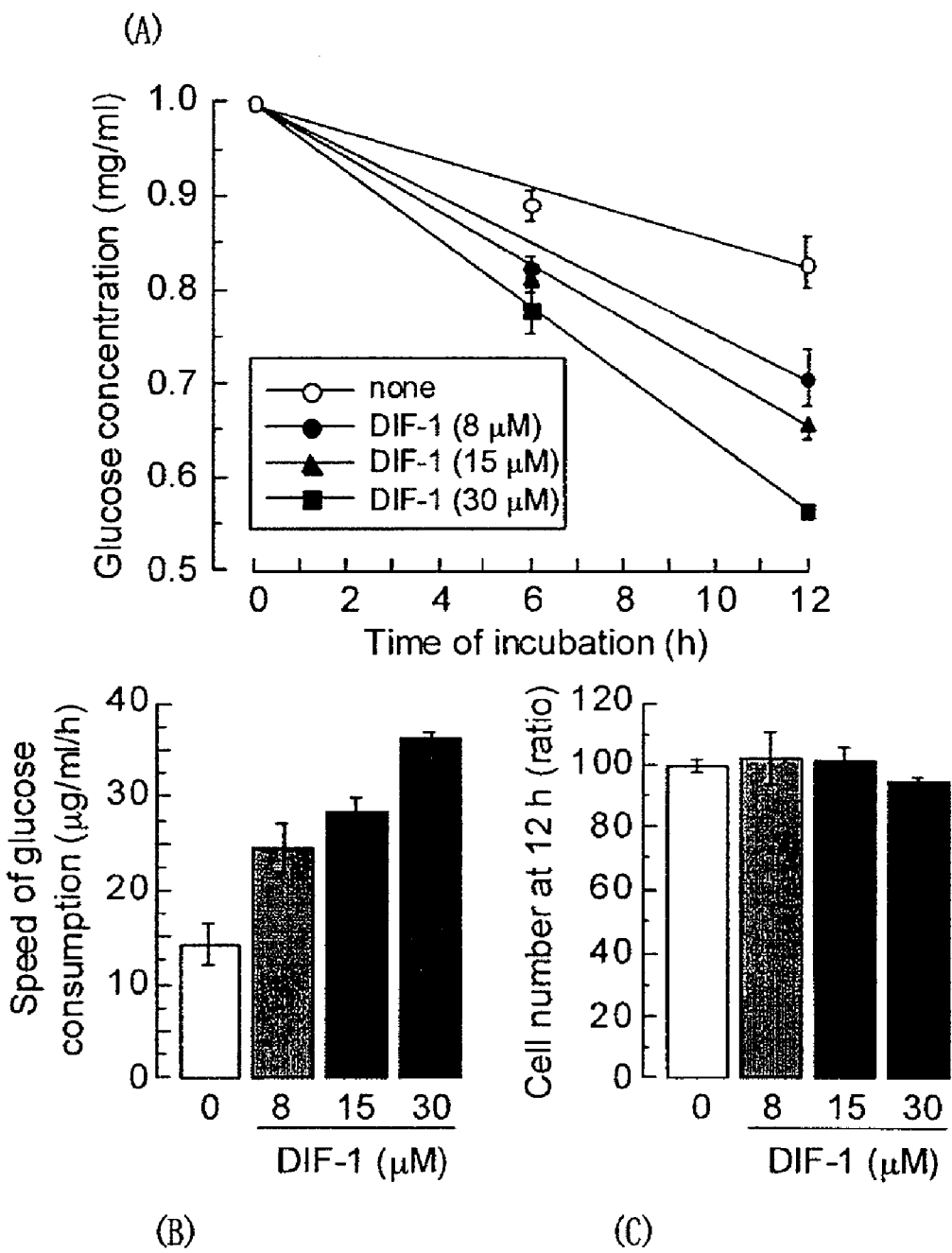
FIG. 4 is a drawing that shows the glucose uptake rate of RGM-1 cells when RGM-1 cells were cultured in the presence of DIF-1. Graph A shows the glucose concentration in the medium after 6- and 12-hour-culture with no addition, or with addition of each concentration of DIF-1. Graph B shows the glucose uptake rate of each kind of the cells and graph C shows the number of cells after the 12-hour-culture.

Similar experiments were performed with RGM-1 cells (isolated from rat gastric mucosa) to evaluate the change in glucose concentration in the medium containing DIF-1 or other compounds (FIG. 4). The data of the graph are mean values and standard deviations (Bars) (n=3) of triplicate samples measured under the same conditions.

As a result, it was found that DIF-1 promotes glucose uptake in a concentration-dependent manner in RGM-1 cells as well without influencing cell number. Furthermore, it was also found that this evaluation system is efficient for measuring glucose uptake-promoting effect of drugs, and is a simple method which can be performed using various kinds of cultured cells.

Example 4

Glucose uptake-promoting activity of DIF-1 derivative compounds in 3T3-L1 cells was evaluated in the same manner as described above. The data of the graph are mean values and standard deviations (Bars) (n=3) of triplicate samples measured under the same conditions.

As a result, it was observed that the compounds shown below exhibited glucose uptake-promoting activity to the extent similar to DIF-1 or to some extent.

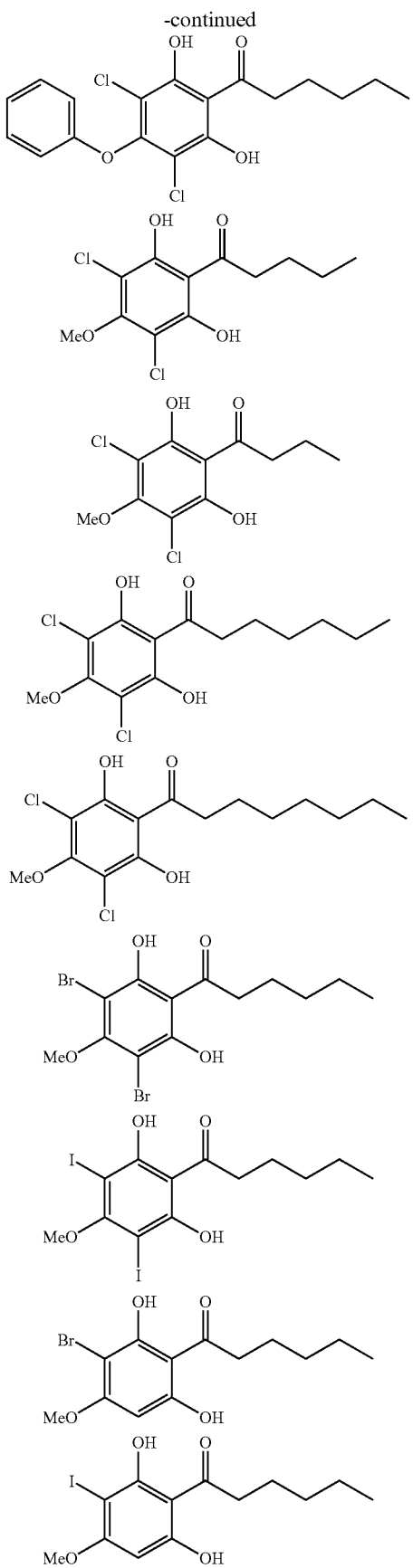

11

-continued

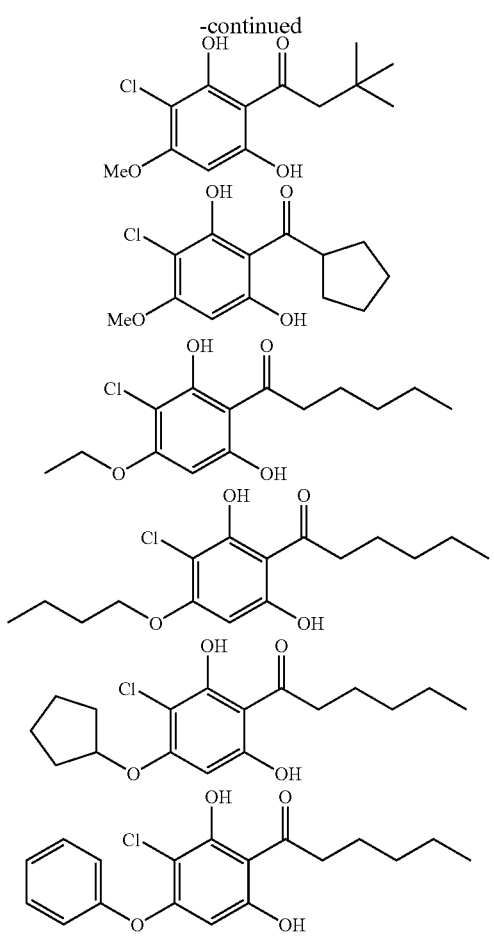

Example 5

Evaluation of Glucose Uptake—Additive Effects with Insulin in Adipocytes

Figure 5:
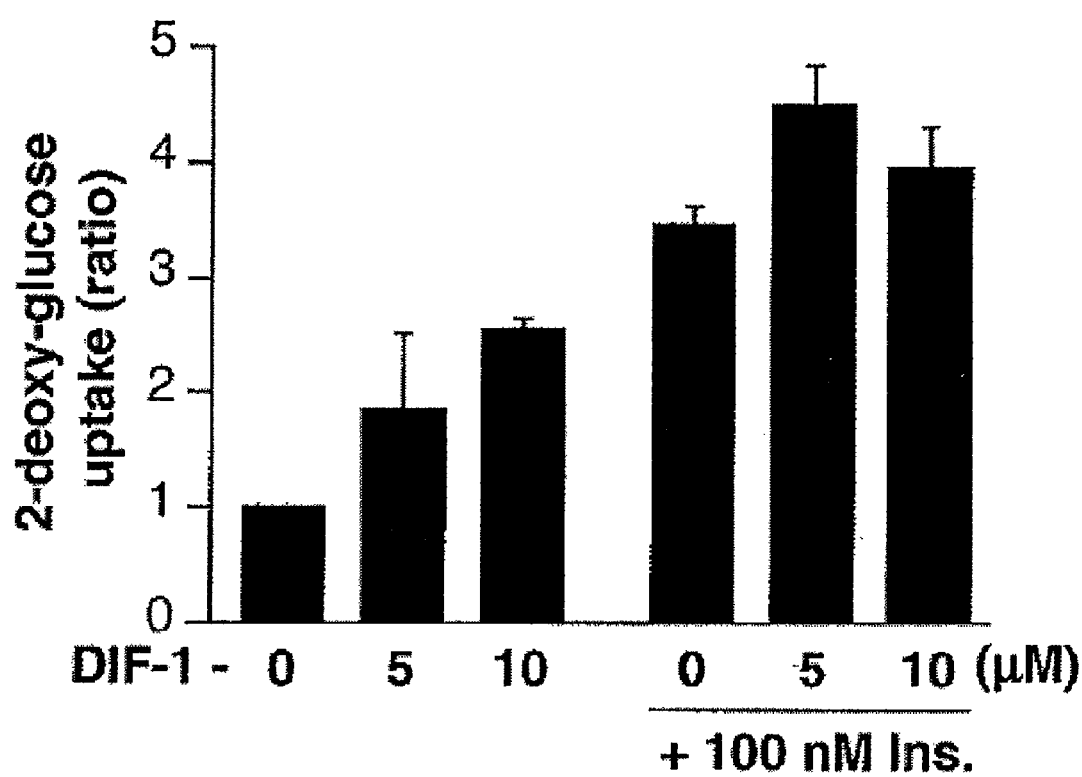
FIG. 5 is a drawing that shows the glucose uptake promoting effect of DIF-1 or DIF-1 and insulin (Ins.) in 3T3-L1 adipocytes.

Confluent 3T3-L1 fibroblasts (cultured in a 12-well plate) were treated with IBMX (3-isobutyl-1-methylxanhine), dexamethasone, and insulin to induce differentiation into 3T3-L1 adipocytes (Student A K, Hsu R Y & Lane M D (1980) J. Biol. Chem. 255, 4745-4750.). The 3T3-L1 adipocytes were cultured in the presence of DIF-1 whose concentration is shown in FIG. 5 for four hours, and 2-deoxy glucose uptake was measured. At the same time, some of the adipocytes were stimulated with 100 nM insulin during cultivation (after 3.5 hours) in the presence of DIF-1, and cultured for another 30 minutes, and glucose uptake of the cells was measured. Each experiment was performed in triplicates, and the mean values thereof were calculated in each experiment. Such experiments were performed twice and the mean values and ½ variance (Bars) of the two experiments (n=2) were plotted in FIG. 5.

As a result, DIF-1 singly promoted glucose uptake in a concentration-dependent manner. Furthermore, relatively low concentration of DIF-1 exhibited an additive effect with insulin. From these results, it is expected that DIF-1 promotes insulin action.

12

Example 6

Figure 6:
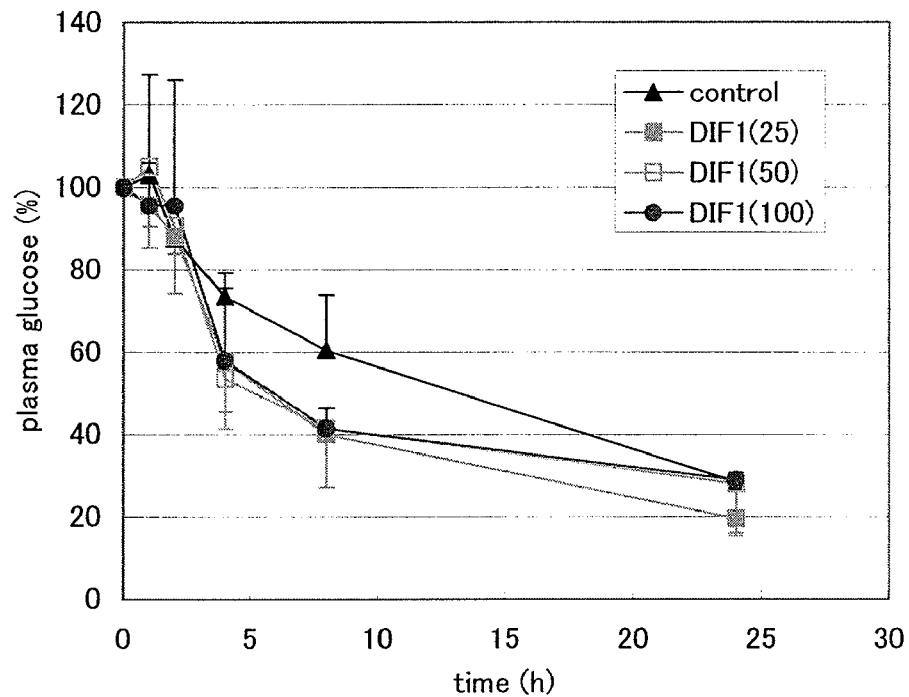
FIG. 6 is a drawing that shows the effects of DIF-1 and DIF-1 (3M) on blood glucose level in KKAy mice.
Figure 6:
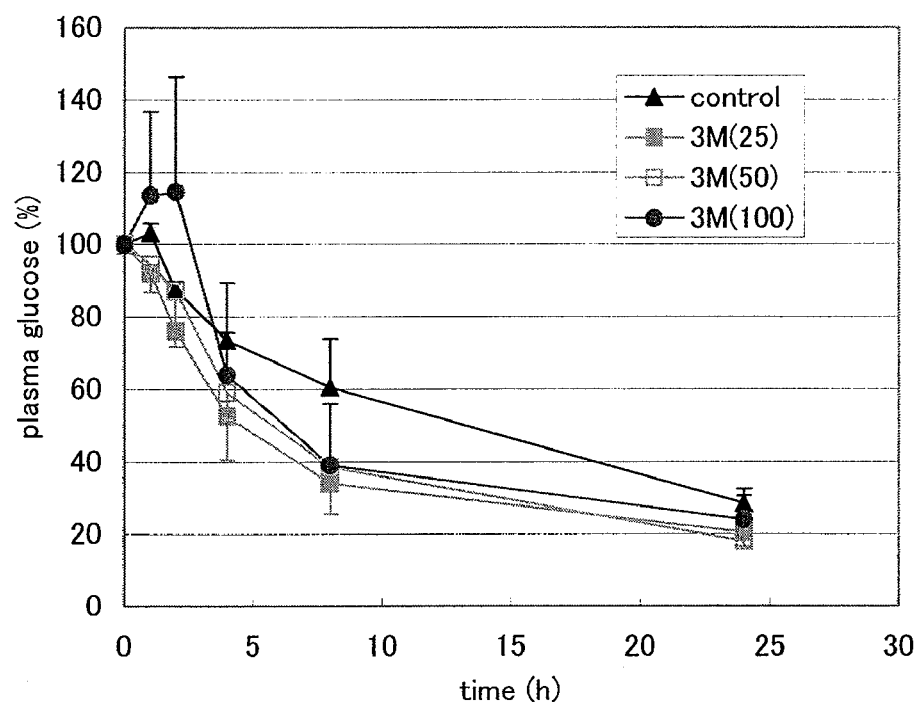

Effect of DIF-1 and DIF-1 (3M) on Blood Glucose Level in KKAy Diabetic Model Mice The in vivo effects of DIF-1 and DIF-1 (3M) were also evaluated with the KKAy diabetic model mice. The drugs were administered intraperitoneally to KKAy mice (male, 13 weeks: Clea Japan) at the concentrations of 25, 50, and 100 mg/kg, respectively, and after free feeding (Time 0), blood glucose level was monitored at the indicated time points (FIG. 6). Each of the experiments used two mice, and the mean values of the relative blood glucose concentrations and ½ variance (Bars)(n=2) were plotted.

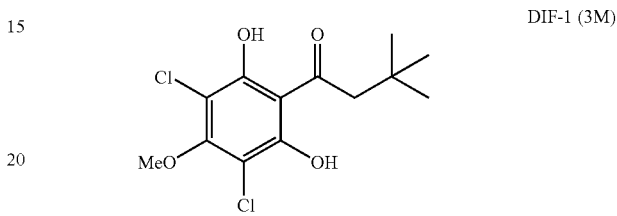

DIF-1 (3M)

As a result, both of DIF-1-administered mice and DIF-1 (3M)-administered mice showed low blood glucose level 4 and 8 hours after administration as compared with the control group (without drugs). No mice died before 24 hours after administration.

INDUSTRIAL APPLICABILITY

The compounds of the present invention have significant activity to promote glucose uptake in various kinds of cells and thus can be used as blood glucose-lowering agent which is effective for treating or preventing diseases such as diabetes and obesity. Furthermore, the compounds lower blood glucose independently from insulin, and thus can also be used for insulin resistant diabetes and obesity. Furthermore, the compounds lower blood glucose reversibly, which enables strict control of blood glucose level.

While the invention has been described in detail with reference to preferred embodiments thereof, it will be apparent to one skilled in the art that these embodiments are not restrictive but exemplifications. Each of the aforementioned documents is incorporated by reference herein in its entirety.

The invention claimed is:

1. A method of lowering blood glucose level in a subject, comprising administering a medicament comprising a compound represented by the formula (I) as an active ingredient to the subject:

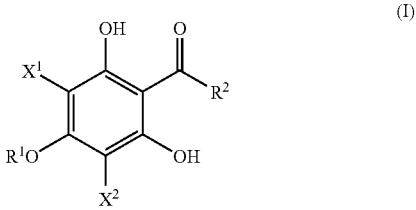

(I)

wherein, $R^1$ and $R^2$ independently represent an aliphatic hydrocarbon group having 1 to 10 carbon atoms or phenyl group, and arbitrary hydrogen atoms on the aliphatic hydrocarbon group and the phenyl group may be replaced by halogen, $X^1$ represents halogen, and $X^2$ represents hydrogen or halogen.

2. A method of treating obesity and/or diabetes in a subject, comprising administering a compound represented by the formula (I) to the subject to ameliorate a symptom of the subject:

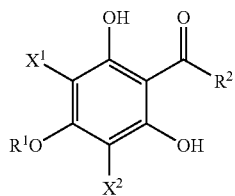

(I)

wherein, $R^1$ and $R^2$ independently represent an aliphatic hydrocarbon group having 1 to 10 carbon atoms or phenyl group, and arbitrary hydrogen atoms on the aliphatic hydrocarbon group and the phenyl group may be replaced by halogen, $X^1$ represents halogen, and $X^2$ represents hydrogen or halogen.

3. The method according to claim 2, wherein said diabetes is insulin resistant diabetes.

* * * * *

UNITED STATES PATENT AND TRADEMARK OFFICE
CERTIFICATE OF CORRECTION

PATENT NO. : 7,846,974 B2
APPLICATION NO. : 11/923064
DATED : December 7, 2010
INVENTOR(S) : Kubohara et al.

Figure 7:
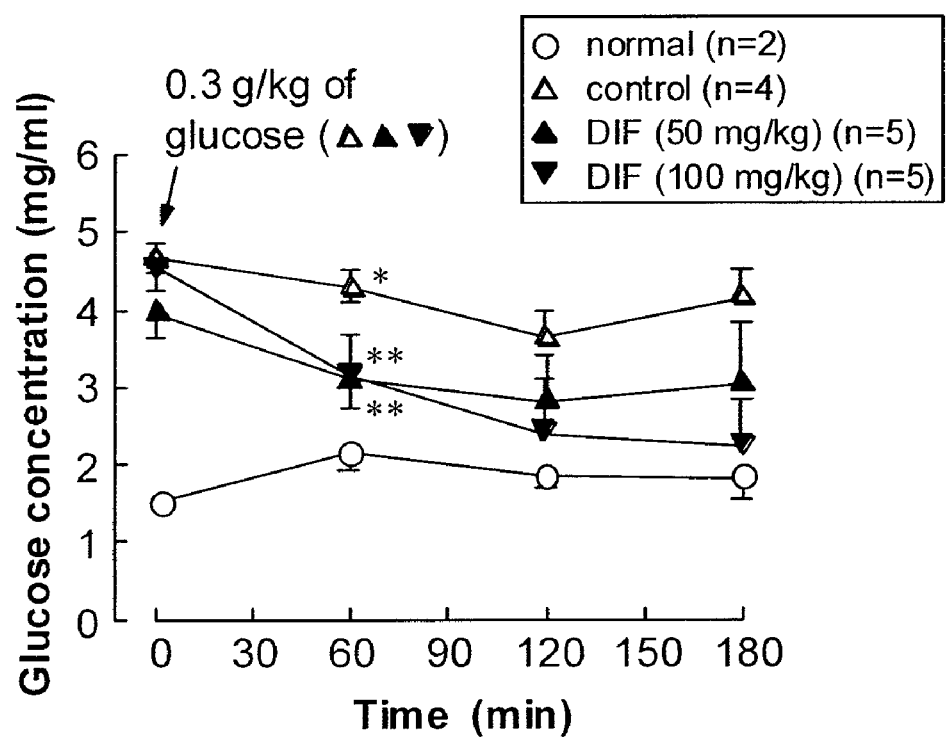
FIG. 7 is a drawing that shows the effect of DIF-1 on blood glucose level of ICR mice.

It is certified that error appears in the above-identified patent and that said Letters Patent is hereby corrected as shown below:

In the Drawings, Sheet 7 of 7, Fig. 7 should be deleted.

Column 2, Lines 66-67, "FIG. 7 is a...level of ICR mice." should be deleted.

Column 6, Line 16, "Other Derivative Compounds—Continued:" should be deleted.

Column 7, Line 17, "ester, chlorobuthanol," should be changed to --ester, chlorobutanol,-- .

Column 11, Line 46, "(3-isobutyl-1-methylxanhine)," should be changed to --(3-isobutyl-1-methylxanthine),--.

Signed and Sealed this
Thirty-first Day of July, 2012

David J. Kappos
*Director of the United States Patent and Trademark Office*